US012217426B2

(12) United States Patent
Piredda et al.

(10) Patent No.: US 12,217,426 B2
(45) Date of Patent: Feb. 4, 2025

(54) METHOD AND SYSTEM FOR MEASURING A MATURATION STAGE USING MRI (71) Applicant: SIEMENS HEALTHCARE GMBH, Erlangen (DE)

(72) Inventors: Gian Franco Piredda, Ecublens (CH); Tobias Kober, Lausanne (CH); Tom Hilbert, Lausanne (CH); Lars Lauer, Neunkirchen (DE)

(73) Assignee: Siemens Healthineers AG, Erlangen (DE)

( * ) Notice: Subject to any disclaimer, the term of this patent is extended or adjusted under 35 U.S.C. 154(b) by 337 days.

(21) Appl. No.: 17/207,963

(22) Filed: Mar. 22, 2021

(65) Prior Publication Data

US 2021/0295521 A1  Sep. 23, 2021

(30) Foreign Application Priority Data

Mar. 20, 2020  (EP) .................................. 20164377

(51) Int. Cl.
*G06T 7/00* (2017.01)
*A61B 5/055* (2006.01)

(52) U.S. Cl.
CPC ............ *G06T 7/0016* (2013.01); *A61B 5/055* (2013.01); *G06T 2207/10088* (2013.01);
(Continued)

(58) Field of Classification Search
CPC ......... G06T 7/0016; G06T 2207/10088; G06T 2207/20081; G06T 2207/20084; G06T 2207/30016; A61B 5/055
(Continued)

(56) References Cited

U.S. PATENT DOCUMENTS

2017/0095180 A1* 4/2017 Na ....................... A61B 5/1076
2018/0074148 A1* 3/2018 Pfeuffer ............... G01R 33/546

FOREIGN PATENT DOCUMENTS

| CN | 109804262 A | * | 5/2019 | ............ A61B 5/0042 |
| CN | 110097968 A | * | 8/2019 | ............. A61B 5/055 |
| EP | 3248543 A1 | * | 11/2017 | ............ A61B 5/0042 |

OTHER PUBLICATIONS

Wang et al., Gray Matter Age Prediction as a Biomarker for Risk of Dementia, Oct. 2019, PNAS, vol. 116, 21213-21218 (Year: 2019).*
(Continued)

*Primary Examiner* — Wednel Cadeau
(74) *Attorney, Agent, or Firm* — Laurence A. Greenberg; Werner H. Stemer; Ralph E. Locher (57) ABSTRACT

A system and a method for measuring a maturation stage of a biological organ are based on quantitative MR maps for the organ. The method includes acquiring with a first interface and for a subject, a quantitative MR map for the organ. The quantitative MR map includes voxels each characterized by a quantitative value. The quantitative value of each voxel represents a measurement of a physical or physiological property of a tissue of the biological organ for the voxel. The method also includes applying to the quantitative map a trained function to estimate the subject organ maturation stage, and the trained function outputting an age. The method provides with a second interface the maturation stage of the organ of the subject as being the output age.

12 Claims, 2 Drawing Sheets

(52) U.S. Cl.
CPC ............... *G06T 2207/20081* (2013.01); *G06T 2207/20084* (2013.01); *G06T 2207/30016* (2013.01)

(58) Field of Classification Search
USPC ........................................................ 382/131
See application file for complete search history.

(56) References Cited

OTHER PUBLICATIONS

Wang et al., Gray Matter Age Prediction as a Biomarker for Risk of Dementia, Oct. 2019, PNAS, vol. 116, 21213-21218 (Year: 2018).*
Cole et al., Predicting Brain Age with Deep Learning from Raw Imaging Data Result in a Reliable and Heritable Biomarker, Mar. 2017, NeuroImage (Year: 2017).*
Tsialios et al., Evaluation of MRI sequences for quantitative T1 brain mapping, 2017, Journal of Physics: Conference Series (Year: 2017).*
Wang et al., Gray Matter Age Prediction as a Biomarker for Risk of Dementia, 2019, PNAS, vol. 116, 21213-21218 (Year: 2018).*
Douglas C. Dean 111 et al., "Estimating the Age of Healthy Infants From Quantitative Myelin Water Fraction Maps" p. 1233-1244, Year: 2015.
Johnny Wang et al: "Gray Matter Age Prediction as a Biomarker for Risk of Dementia", Proceedings of the National Academy of Sciences, vol. 116, No. 42, Oct. 1, 2019 (Oct. 1, 2019), pp. 21213-21218, XP055716797, ISSN: 0027-8424, DOI: www.pnas.org/cgi/doi/10.1073/pnas.1902376116.
James H. Cole et al., "Predicting Age Using Neuroimaging: Innovative Brain Ageing Biomarkers", www.researchgate.net/publication/320582159, Article in Trends in Neurosciences Oct. 1, 2017, TINS 1342 No. of pp. 1-10.
Tzu-Wei Huang et al., "Age Estimation from Brain MRI Images Using Deep Learning", p. 849-852, 978-1-5090-1172-8/17/$31.00 © 2017 IEEE.
Jesus Pujol et al., "Delayed myelination in children with developmental delay detected by volumetric MRI", www.elsevier.com/locate/ynimg, NeuroImage 22 (2004) 897-903, revised Dec. 19, 2003; accepted Jan. 16, 2004, Available online Apr. 8, 2004.
Gian Franco Piredda et al., "Measuring brain maturation with quantitative MRI".
Sylvain Eminian et al., Article "Rapid high resolution T1 mapping as a marker of brain development: Normative ranges in key regions of interest", https•//doi.org/10_1371/journal.pone.0198250, Editor: Nader Pouratian, Published: Jun. 14, 2018, p. 1/16.
Mahdieh Shabanian et al., "Classification of Neurodevelopmental Age in Normal Infants Using 3D-CNN based on Brain MRI".
Leila Keshavarz Afshar et al., "Age Prediction based on Brain MRI Images using Extreme Learning Machine", 2019 $7^{th}$ Iranian Joint Congress on Fuzzy and Intelligent Systems (CFIS), [retrieved on Apr. 15, 2019], Jan. 29, 2019, pp. 1-5.
Katja Franke et al., Article "Estimating the age of healthy subjects from $T_1$-weighted MRI scans using kernel methods: Exploring the influence of various parameters", journal homepage: www.elsevier.com/ locate/ynimg, Available online Jan. 11, 2010, p. 883-892.
Pierpaoli, Carlo et al; "Quantitative Brain MRI"; Guest Editorial; vol. 21; No. 2; published: Apr. 1, 2010; p. 63; XP093135960.
Inglese, Matilde et al; "Quantitative MRI: Hidden Age-Related Changes in Brain Tissue"; Topics in magnetic resonance imaging; published: Dec. 1, 2004; vol. 15; No. 6; XP093135965; pp. 355-363.
Callaghan, Martina F. et al; "Widespread age-related differences in the human brain microstructure revealed by quantitative magnetic resonance imaging"; Neurobiology of Aging; vol. 35; No. 8; published: Feb. 15, 2014; pp. 1862-1872; XP028654937.
Pirpamer, Lukas et al; "Determinants of iron accumulation in the normal aging brain"; Neurobiology of Aging; vol. 43; published: Apr. 13, 2016; pp. 149-155; XP029561336.

\* cited by examiner

METHOD AND SYSTEM FOR MEASURING A MATURATION STAGE USING MRI

CROSS-REFERENCE TO RELATED APPLICATION

This application claims the priority, under 35 U.S.C. § 119, of European Patent Application EP20164377.2, filed Mar. 20, 2020; the prior application is herewith incorporated by reference in its entirety.

BACKGROUND OF THE INVENTION

Field of the Invention

The present invention relates, in general, to imaging techniques for imaging biological objects, such as tissues, using Magnetic Resonance Imaging (MRI). More specifically, the present invention is directed to methods and systems for measuring a maturation stage of biological tissue of an organ using MRI.

Determining the maturation stage of an organ might be important for the determination of potential diseases. For instance, it is known that post-natal periods are crucial for the maturation of brain tissue, the structural and functional remodeling of which are associated with the development of cognitive and motor abilities. In this field, and complementary to the fast and inexpensive head circumference assessment, MRI has become a routine diagnostic modality in specialized centers for evaluating normal structural and metabolic development of the brain in infants and older children. In fact, besides the clear increase in size, patterns of brain development that can be probed with MRI which have been identified involve—among others—the myelination of white (WM) and grey matter (GM) tissues, neuronal proliferation and axonal pruning. In particular, the development of psychomotor delay and/or other neurological disorders have been associated with the delayed spatiotemporal maturation of axonal myelination [1]. Even in adult life, the human brain shows typical age-dependent changes. Hence, a clinical biomarker that is sensitive to this tissue reorganization and maturation would be of help to detect atypical brain development and to complement the complex—and often only qualitative—assessment and interpretation of pediatric and adult brain images.

In the past years, different brain features which can be identified by structural MRI have been proposed as estimates of brain age, with most of the applications focusing on the adult brain. Franke, et al. [2] were for instance able to predict the age of adult subjects between 19 and 86 years of age with a mean absolute error (MAE) of 4.98 years by training machine learning classifiers as support vector machines (SVMs) and relevance vector regression (RVMs) with image intensities of T1-weighted acquisitions. Cole, et al. [3] trained a convolutional neural network (CNN) to accurately predict the chronological age of healthy adults from grey matter volumetric maps, achieving a MAE of 4.16 years. Training a similar CNN with native T1-weighted brain images, Huang, et al. [4] achieved a MAE of 4 years.

In infants, a similar approach based on 3D CNN was investigated by Shabanian, et al. [5] to estimate the age in subjects from 8 days to 3 years based on brain T1-weighted, T2-weighted and PD-weighted MR images. Starting from more quantitative measurements, i.e. myelin water fraction maps, Dean, et al. [6] developed a framework to accurately map voxel-wise estimates of brain age in WM tissues of infants between 3 and 48 months of age by using a probabilistic developmental model following the Gompertz growth curve.

Unfortunately, the previously cited techniques are not very sensitive to microstructural changes, but mostly sensitive to morphological changes. It is therefore desirable to find an improved method and a system capable of providing a quantitative assessment of an organ maturation stage.

BRIEF SUMMARY OF THE INVENTION

It is accordingly an object of the invention to provide a method and a system for quantitative assessment of an organ maturation stage, which overcome the hereinafore-mentioned disadvantages of the heretofore-known methods and systems of this general type. Dependent claims present further advantages of the invention.

More specifically, the present invention proposes to derive a quantitative assessment of an organ maturation stage, e.g. the brain, by estimating a subject age according to a measurement of quantitative organ parameters as e.g. T1 values. While the present description will mainly focus on the example of a brain as the organ, it has to be noted that the described concept might also apply to any other organ or organ group such as e.g. the liver, pancreas, prostate, knee/shoulder cartilage, spine, among others.

The present invention concerns in particular a computer-implemented method for measuring a maturation stage of a biological organ, such as a brain, the method comprising:
  acquiring with a first interface and for a subject, one or several quantitative MR maps for the organ, wherein each quantitative MR map includes voxels each characterized by a quantitative value, wherein the quantitative value of each voxel represents a measurement of a physical or physiological property of a tissue of the biological organ for the voxel;
  if required, i.e. optionally, applying, preferentially automatically, to each of the acquired quantitative MR maps a segmentation process configured for segmenting the biological organ into different regions each characterized by a single tissue-type. This step is notably only required for non-homogeneous biological organs including different tissue types. For instance, for a liver, which is a substantially homogeneous organ, this step is not required, while it would be required for a non-homogeneous organ like the brain for differentiating the gray matter (GM), white matter (WM), and the cerebrospinal fluid (CSF);
  applying to the quantitative map a trained function, preferentially a trained random forest regression model, to estimate the subject organ maturation stage, wherein the trained function outputs an age; and
  providing with a second interface the maturation stage of the subject's organ as being the output age.

The present invention also concerns a computer-implemented method for providing a trained function for estimating the maturation stage of an organ, the method comprising:
  receiving or acquiring through a first interface an input dataset, wherein the input dataset includes quantitative MR maps for the organ in a representative population (e.g. young healthy subjects), wherein each quantitative MR map includes voxels the quantitative value of which represents a measurement of a physical or physiological property of a tissue of the biological organ for a subject of the representative population;
  receiving through a second interface an output dataset, wherein the output dataset includes, for each quantitative MR map, the age of the subject for which the quantitative MR map has been obtained, making it therefore possible to associate to each quantitative MR map the age of the subject for which the map has been obtained;

automatically creating an input training dataset, wherein
  if required, i.e. optionally, applying, preferentially automatically, a segmentation process to each of the quantitative MR maps, wherein the segmentation process is configured for classifying, preferentially automatically classifying, the different tissues and optionally structures included within the organ in order to segment the organ into different regions. The segmentation process used during the present training phase is preferentially the same as the segmentation process used for evaluating the maturation stage of a new subject using the trained function of the previously presented computer-implemented function;
  for each quantitative MR map, automatically determining from the voxels of the quantitative MR map at least one characteristic quantitative value for at least one region, preferentially for each region of the organ, the characteristic quantitative value being for instance the median quantitative value of the voxels belonging to a region or, for example, the total volume of that region. In the case of a homogeneous organ, the region can be the whole organ;
  automatically filling the input training dataset with the characteristic quantitative values obtained for each region for each quantitative MR map, wherein each region of each quantitative MR map is related to (i.e. associated to or paired with) a subject age;
automatically training a function, e.g. a random forest regression model, based on the input training dataset and the output dataset, wherein the function is trained to estimate the organ maturation stage from the characteristic quantitative value(s) determined for at least one region, e.g. for each region or a set of preferred regions, as stored in the input training dataset and from the corresponding age of the subject for which the characteristic quantitative value has been obtained, as stored in the output dataset, wherein a training computation unit is used for training the function from the input training dataset and the output dataset, wherein the training computation unit is preferentially configured for using a machine learning algorithm; and
providing the trained function with a third interface.

The present invention also concerns a training system comprising:
  a first interface configured for receiving an input dataset, wherein the input dataset includes the quantitative MR maps for the organ in a representative population;
  a second interface configured for receiving an output dataset, wherein the output dataset includes, for each quantitative MR map, the age of the subject for which the quantitative MR map has been obtained;
  a training computation unit configured for creating the input training dataset and for training the previously described function based on the input training dataset and the output dataset, wherein the training uses a machine learning algorithm configured for estimating the organ maturation stage; and
  a third interface for providing the trained function.

Finally, the present invention also concerns a system for automatically estimating a maturation stage of an organ of a subject, the system comprising:
  a connection to an MRI apparatus for acquiring a quantitative MR map for the organ;
  a memory for storing each of the acquired quantitative MR maps;
  a control unit including a processor, the control unit being configured for automatically estimating the maturation stage of the organ of the subject;
  a display for displaying the estimated maturation stage obtained for the organ and, optionally, comparing the obtained estimation to the actual/real age of the organ;
characterized in that the control unit is configured for applying a function trained by a machine learning algorithm to the acquired quantitative MR map in order to output an estimation of the maturation stage of the organ.

In particular, the system according to the invention may automatically calculate a difference between the actual/real age of the organ (which corresponds to the age of the subject) and its estimated age (i.e. the estimated maturation stage). Advantageously, the difference represents useful information to discern the degree of maturation of the organ of a subject under analysis.

The foregoing has broadly outlined the features and technical advantages of the present disclosure so that those skilled in the art may better understand the detailed description that follows. Additional features and advantages of the disclosure will be described hereinafter that form the object of the claims. Those skilled in the art will appreciate that they may readily use the concept and the specific embodiment disclosed as a basis for modifying or configuring other structures for carrying out the same purposes of the present disclosure. Those skilled in the art will also realize that such equivalent constructions do not depart from the spirit and scope of the disclosure as defined by the set of claims.

Other features which are considered as characteristic for the invention are set forth in the appended claims.

Although the invention is illustrated and described herein as embodied in a method and a system for measuring a maturation stage using MRI, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
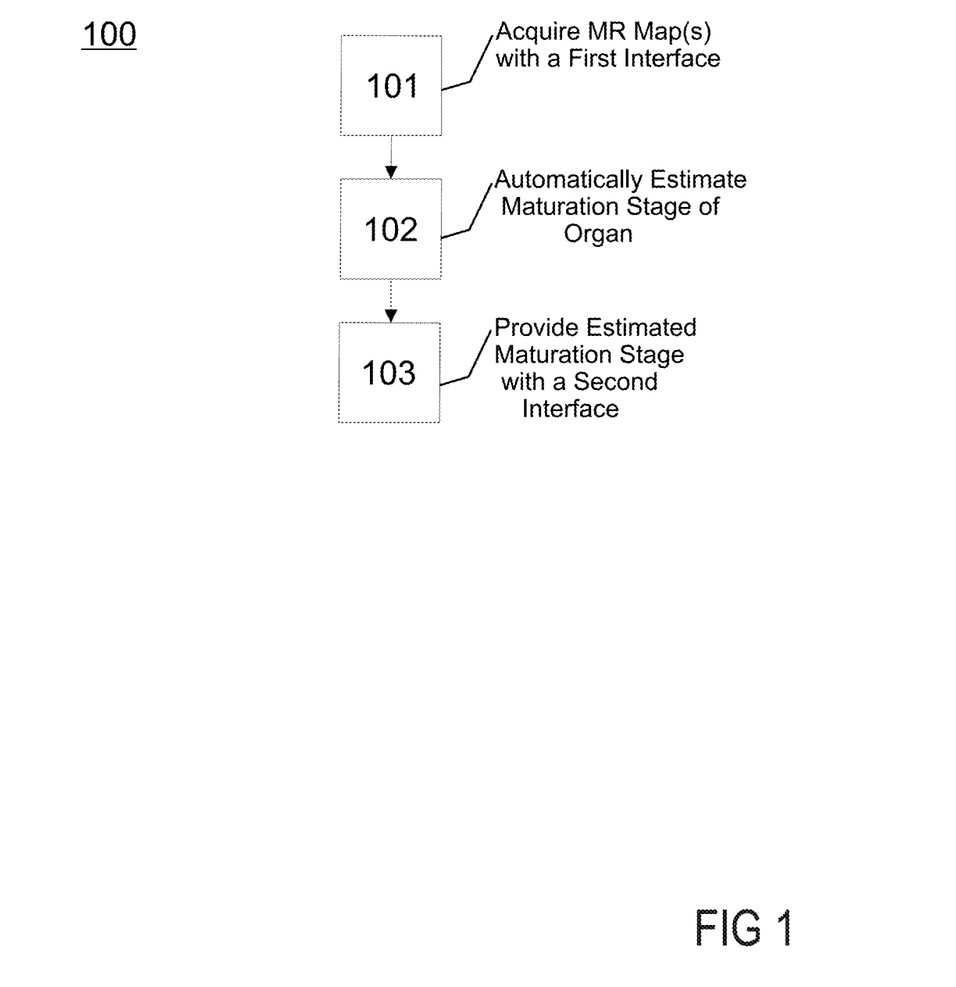
FIG. 1 is a flowchart of a method for estimating a maturation stage of an organ according to the invention.

Referring now in detail to the figures of the drawings, it is seen that FIGS. 1 and 2, discussed below, and the various embodiments used to describe the principles of the present disclosure in this application are by way of illustration only and should not be construed in any way to limit the scope of the disclosure. Those skilled in the art will understand that the principles of the present disclosure may be implemented in any suitably disposed device. The numerous innovative teachings of the present application will be described with reference to exemplary non-limiting embodiments.

Figure 2:
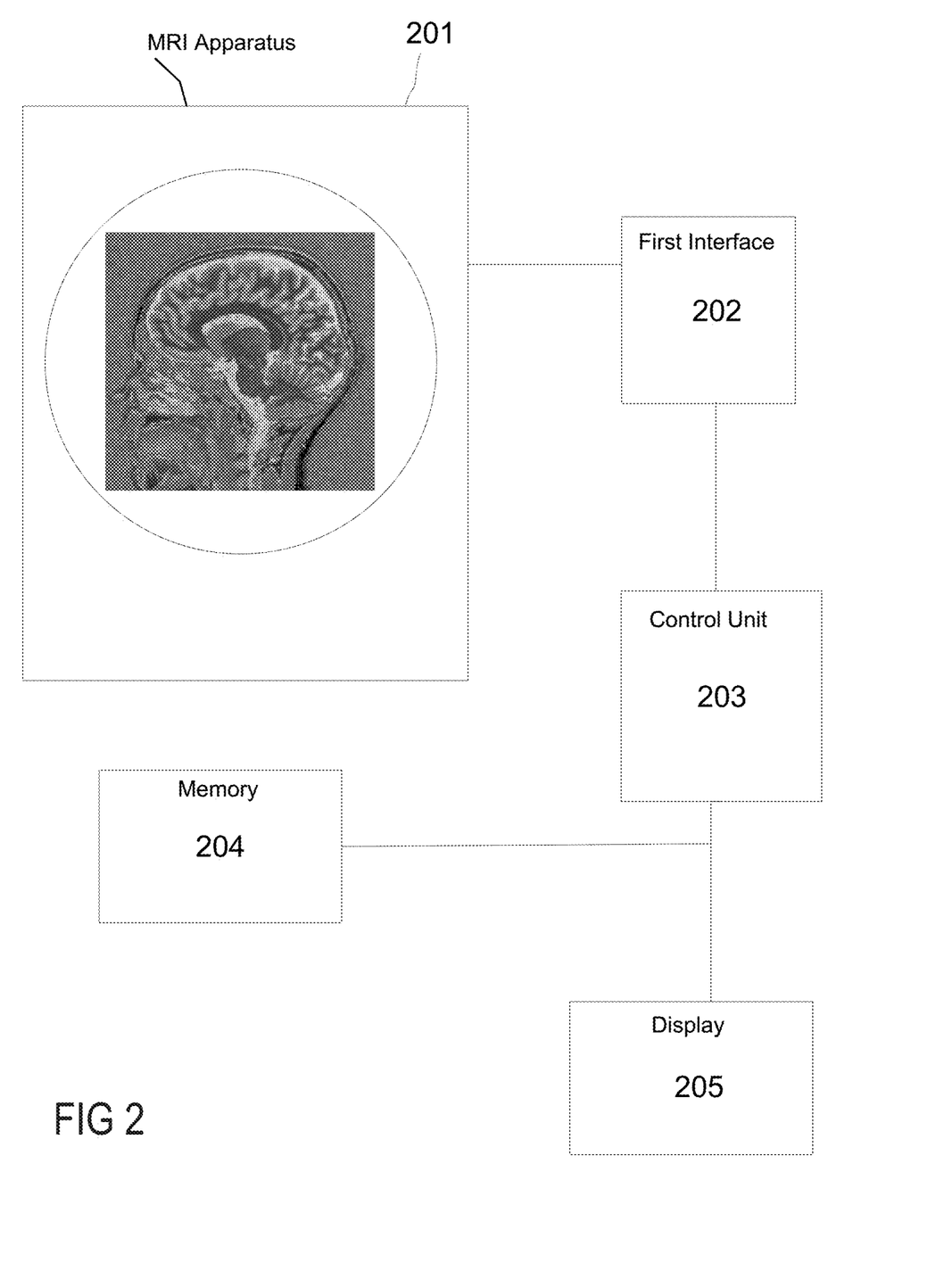
FIG. 2 is a block diagram of a system for implementing the method.

The method according to the invention will now be described in more detail by reference to FIG. 1 and FIG. 2, wherein FIG. 1 discloses the different steps of the method 100 carried out by a preferred embodiment of the system according to the invention which is illustrated in FIG. 2.

At step 101, the system according to the invention acquires with a first interface 202 and for a subject, one or several quantitative MR maps 200 for an organ of the subject. The organ is for instance the brain or any other organ that might be characterized by different maturation stages. Preferentially, the first interface 202 is connected to an MRI apparatus 201 for acquiring each of the quantitative MR maps for the organ. The quantitative MR map is a map including voxels having values which represent a measurement of a physical or physiological property of a tissue of the organ for the concerned voxel. A quantitative MR map according to the invention might be of one of the following types:
- a T1 quantitative map;
- a T2 quantitative map;
- a T2* quantitative map;
- a diffusion coefficient map;
- a myelin map;
- a microstructural and/or volumetric quantification map;
- a morphometry measurement map, the morphometry measurement map providing a measurement of a physical property (i.e. a volume) transferred into a metric (e.g. in mm3 per region based on the segmentation of the organ).

If a segmentation is required, then the segmentation process is preferentially fully automated, but a manual segmentation is also compatible with the present invention. The segmentation process used for segmenting the quantitative maps of the training phase and for segmenting the quantitative map(s) acquired for a subject for which the maturation stage of an organ has to be evaluated using the trained function are preferentially the same. In particular, the trained function is configured for automatically identifying an organ region, e.g. the different segmented regions, within a quantitative map for the organ and to determine or estimate from the characteristic quantitative value(s) that has(have) been obtained for the region(s) during the training phase the output age which is an estimation of the maturation stage of the organ or organ region under examination.

Preferentially, several quantitative MR maps might be acquired for the same subject, wherein each (or at least two), quantitative MR map(s) is(are) of a different type. The acquired quantitative MR map is then preferentially stored in a memory 204 of the system according to the invention.

At step 102, a control unit 203 including a processor is configured for automatically estimating the maturation stage of the organ of the subject. The maturation stage is the age of the organ as obtained (i.e. evaluated) by the control unit 203 from the acquired quantitative MR map(s). The maturation stage may differ from the real age of the organ, i.e. the age of the subject. For the estimation, the control unit 203 applies a trained function to the acquired quantitative map(s), the trained function outputting the maturation stage which is the estimated age of the organ. Different trained functions might be used for estimating the maturation stage. For instance, the control unit 203 may use:
- a trained random forest regression model;
- a trained general linear model (GLM);
- a trained support vector machine (SVM);
- a trained relevance vector machine (RVM);
- a trained neural network; or
- any other predictive model that would be suitable and capable of providing an estimation of the maturation stage from the acquired MR quantitative map(s).

At step 103, the control unit 203 provides the estimated maturation stage with a second interface. The second interface is for instance connected to a display 205, so that the age output by the trained function is displayed as the estimated maturation stage obtained for the organ.

According to the present invention, a training system is used for training the function. The training system may include a first interface, which can be the same as, or different from, the first interface 202 of the system according to the invention, a second interface, which can be a touch-screen display or a keyboard, and a training computation unit, which can be the control unit 203.

The first interface is configured for receiving an input dataset including quantitative MR maps for the organ, wherein the quantitative MR maps have been obtained for a representative population by use, for instance, of the MRI apparatus 201. For each subject of the population, the acquired quantitative maps might be quantitative maps of the same and/or of different types. The second interface is configured for receiving an output dataset including, for each of the acquired quantitative MR maps, the age of the subject for which the quantitative MR map has been obtained. In particular, the training system may include a database wherein each input data of the input dataset, i.e. each quantitative MR map, is associated directly or in a modified form (e.g. in the form of the input training dataset presented later on) to output data of the output dataset, i.e. to an age of a subject.

The acquired quantitative MR maps are first processed by the training computation unit in order to create an input training dataset. For this purpose, the training computation unit automatically determines at least one characteristic quantitative value from the voxels of one or several regions of the quantitative MR map. Preferentially the regions are obtained after applying a segmentation process to each quantitative MR map by the training computation unit, wherein the segmentation process enables the training computation unit to divide the quantitative MR map into one or several regions which include each a single type of tissue. In particular, the training computation unit may perform, preferentially automatically, a segmentation of each quantitative MR map of the organ into different regions, notably if the organ is considered as non-homogeneous, wherein each region is characterized by a single type of tissue of the organ. For the same tissue type, multiple regions might be defined within the same quantitative MR map. In other words, the training computation unit is preferentially configured for dividing each quantitative MR map into a set of regions, wherein the regions can be predefined in function of a structure of the organ, wherein the regions are preferentially non-overlapping, and wherein each region includes a single type of tissue of the organ. Then, for each or a preferred set of the regions within each of the quantitative MR maps, the training computation unit automatically determines the characteristic quantitative value(s) from the voxels of the quantitative MR map belonging to the region. The characteristic quantitative value(s) might for instance be one or more of the following metrics:
- a median quantitative value calculated for the voxels of the considered organ region;
- a mean quantitative value calculated for the voxels of the considered organ region;

a standard deviation value calculated for the voxels of the considered region;

a mode quantitative value calculated for the voxels of the considered organ region;

a maximum voxel value calculated for the voxels of the considered region;

a coefficient of variation calculated for the voxels of the considered region;

the absolute or normalized volume of the considered region;

other metrics that change with age and which could be extracted from the voxel quantitative values for each region and used for the organ age prediction.

If several quantitative MR maps are acquired for the subject, e.g. several quantitative MR maps of the same type and/or of a different type, then the training computation unit may calculate the characteristic quantitative value(s) for each region of the organ within each of the quantitative MR maps, wherein if different types of quantitative MR maps are processed by the training computation unit, then different types of characteristic quantitative values might be obtained, for instance a first type being a median voxel quantitative value for a T1 relaxation map and a second type being a median voxel quantitative value for a T2 relaxation map and/or any of the other metrics that could be obtained from the voxel values of the regions of the T2 relaxation map. Optionally, the number of regional characteristic quantitative values under consideration might be reduced to eliminate any correlation between characteristic quantitative values, and thus a potential redundancy. Such a dimensionality reduction could be achieved by using techniques such as principal component analysis (PCA), Linear Discriminant Analysis (LDA), among others. In addition to the quantitative maps, more conventional volumetric measurements could be included in the prediction of the maturation stage.

According to the present invention, the training computation unit is configured for automatically creating the input training dataset from the characteristic quantitative values obtained for each region of each quantitative MR map of the organ and to associate, e.g. in the database, input training data that is the characteristic value obtained for a region with output data that is the age of the subject from which the quantitative MR map originated. The input training dataset can therefore be populated with characteristic quantitative values determined each for a region of the organ, or with a set of characteristic quantitative values determined for a set of preferred regions of the organ among all regions of the organ, wherein each input training data of the input training dataset, i.e. each characteristic quantitative value obtained for a region (or for a preferred region), is then paired by the training computation unit with output data, i.e. a subject age.

Once the input training dataset has been created by the training computation unit, then the latter automatically trains the function (or model) in charge of the prediction of the maturation stage of the organ. For this training, the function received as input is the input training dataset and as output is the age of each subject, wherein each input training data is paired to output data. At the end of the training, the trained function enables estimating the organ maturation stage from one or several characteristic quantitative values measured within a quantitative MR map for at least one region of the organ.

Finally, the training computation unit provides the trained function with a third interface. Then, the control unit 203 uses the trained function for evaluating the maturation stage of the organ of a (new) subject upon acquisition of a quantitative MR map for the (new) subject and applying the trained function to the quantitative MR map, or to a region of the quantitative map, obtained by using the MRI apparatus for the (new) subject.

In particular, it has been shown that acquiring whole-brain quantitative 3D T1 map with MP2RAGE sequence at 1.5 T for a cohort of 70 young healthy subjects, segmenting each acquired map into 46 regions of interest (ROI), and automatically calculating median T1 values for each ROI, enabled to train a random forest regression algorithm (notably a model with 101 trees, 4 splits at each node) to learn the age of the healthy subjects from the collection of regional T1 values, and gave rise to a correlation of 0.93 between predicted and actual age values of subjects.

To conclude, the present invention proposes to use quantitative MR imaging (i.e. parametric mapping and morphometry) to estimate a maturation stage of an organ. The main advantage of the proposed solution is its sensitivity towards the microstructural changes that the brain/organ of interest undergoes through development and not only morphological changes. In addition, the necessary measurements and post-processing necessary to produce the estimation can be easily obtained at an MRI scanner.

LIST OF CITATIONS

[1] Pujol J, López-Sala A, Sebastian-Gallés N, et al. Delayed myelination in children with developmental delay detected by volumetric MRI. Neuroimage. 2004; 22(2): 897-903.

[2] Franke, K., Ziegler, G., Klöppel, S., Gaser, C., 2010. Estimating the age of healthy subjects from T1-weighted MRI scans using kernel methods: Exploring the influence of various parameters. Neuroimage 50, 883-892.

[3] Cole, J. H., Poudel, R. P. K., Tsagkrasoulis, D., Caan, et al., 2017. Predicting brain age with deep learning from raw imaging data results in a reliable and heritable biomarker. Neuroimage 163, 115-124.

[4] Huang, T. W., Chen, H. T., Fujimoto, R., et al., 2017. Age estimation from brain MRI images using deep learning, in: Proceedings—International Symposium on Biomedical Imaging. pp. 849-852.

[5] Shabanian, M., Eckstein, E. C., Chen, H., DeVincenzo, J. P., 2019. Classification of Neurodevelopmental Age in Normal Infants Using 3D-CNN based on Brain MRI. arXiv 2019.

[6] Dean, D. C., O'Muircheartaigh, J., Dirks, H., et al., 2015. Estimating the age of healthy infants from quantitative myelin water fraction maps. Hum. Brain Mapp. 36, 1233-1244.

The invention claimed is:

1. A computer-implemented method for measuring a maturation stage of a biological subject organ based on quantitative MR (Magnetic Resonance) maps for the organ, the method comprising:

acquiring with a first interface and for a subject, several quantitative MR maps of different types for the organ, the quantitative MR map including voxels each characterized by a quantitative value, the quantitative value of each voxel representing a quantitative measurement of a physical or physiological property, being a physical parameter, of a tissue of the biological organ for the voxel;

applying to each of the acquired quantitative MR maps a segmentation process configured for segmenting the biological organ into different regions each characterized by a single organ tissue type;

using the several quantitative MR maps as input to a trained function to estimate the subject organ maturation stage, the trained function being configured to calculate a characteristic quantitative value for each region of the organ within each of the quantitative MR maps, the trained function being trained for estimating the organ maturation stage from the characteristic quantitative value determined for each region or a set of preferred regions, the trained function outputting an age;

the segmentation process being applied before applying the trained function; and providing with a second interface the maturation stage of the organ of the subject as being the output age.

2. The method according to claim 1, which further comprises selecting a type of the quantitative MR map as of one:
- a T1 quantitative map; or
- a T2 quantitative map; or
- a T2* quantitative map; or
- a diffusion coefficient map; or
- a myelin map; or
- at least one of a microstructural or volumetric quantification map; or
- a morphometry measurement map.

3. The method according to claim 1, which further comprises selecting the trained function as:
- a trained random forest regression model; or
- a trained general linear model; or
- a trained support vector machine; or
- a trained relevance vector machine; or
- a trained neural network; or
- a predictive model configured for providing an estimation of the maturation stage from the acquired MR quantitative map(s).

4. The method according to claim 3, which further comprises acquiring the several quantitative MR maps for an identical subject.

5. A computer-implemented method for providing a trained function for estimating the maturation stage of a biological organ, the method comprising:

receiving an input dataset through a first interface, the input dataset including several quantitative MR (Magnetic Resonance) maps of different types for the organ in a representative population, each quantitative MR map including voxels having a quantitative value representing a quantitative measurement of a physical or physiological property, being a physical parameter, of a tissue of the biological organ for a subject of the representative population;

receiving through a second interface an output dataset, the output dataset including, for each quantitative MR map, the age of the subject for which the quantitative MR map has been obtained;

automatically creating an input training dataset, wherein a segmentation process is applied to each quantitative MR map, the segmentation process being configured to classify the different tissues included within the organ in order to segment the organ into different regions, each region characterized by a single organ tissue type, at least one characteristic quantitative value being determined for each region of each quantitative MR map from the voxels of the quantitative MR map, and the input training dataset being populated with the characteristic quantitative values obtained for each region of each quantitative MR map;

training a function based on the input training dataset and the output dataset with a training computation unit, using the several quantitative MR maps as input to the trained function for calculation of the age, the function being trained to estimate the organ maturation stage from the characteristic quantitative value(s) determined for each region, or a set of preferred regions, and from the age of the subject for which the characteristic quantitative value has been obtained;

the segmentation process being applied before applying the trained function; and providing the trained function with a third interface.

6. The computer-implemented method according to claim 5, which further comprises providing the acquired quantitative maps as quantitative maps of at least one of an identical type or a different type.

7. The computer-implemented method according to claim 5, which further comprises selecting the characteristic quantitative value(s) as one or more metric as follows:
- a median voxel quantitative value calculated for the voxels of the considered organ region; or
- a mean voxel quantitative value calculated for the voxels of the considered organ region; or
- a standard deviation value calculated for the voxels of the considered region; or
- a mode quantitative value calculated for the voxels of the considered organ region; or
- maximum voxel value calculated for the voxels of the considered region; or
- a coefficient of variation calculated for the voxels of the considered region; or
- an absolute or normalized volume of the considered region; or
- age dependent metrics extracted from the voxel quantitative values for each region for the organ age prediction.

8. The computer-implemented method according to claim 2, which further comprises reducing a number of regional characteristic quantitative values under consideration to eliminate any correlation between characteristic quantitative values.

9. A training system for training a function for estimating the maturation stage of an organ, the training system comprising:

a first interface configured for receiving an input dataset, the input dataset including several quantitative MR (Magnetic Resonance) maps of different types for the organ in a representative population, each quantitative MR map including voxels having a quantitative value representing a quantitative measurement of a physical or physiological property, being a physical parameter, of a tissue of the biological organ for a subject of the representative population;

a second interface configured for receiving an output dataset, the output dataset including, for each quantitative MR map, an age of the subject for which the quantitative MR map has been obtained;

a training computation unit configured for creating an input training dataset from the input dataset, wherein a segmentation process is applied to each quantitative MR map, the segmentation process being configured to classify the different tissues included within the organ in order to segment the organ into different regions, each region characterized by a single organ tissue type;

said training computation unit additionally configured to train a function based on the input training dataset and the output dataset, the training using a machine learning algorithm configured for estimating the organ maturation stage, the several quantitative MR maps being applied as input to the trained function for calculation of the age, the function being configured to calculate a characteristic quantitative value for each region of the organ within each quantitative MR map, and the function being trained to estimate the organ maturation stage from the characteristic quantitative value determined for each region or a set of preferred regions;

said training computation unit configured to apply the segmentation process before applying the trained function; and a third interface for providing the trained function.

10. A system for automatically measuring a maturation stage of a biological organ of a subject, the system comprising:

a connection to an MRI (Magnetic Resonance Imaging) apparatus configured for acquiring several quantitative MR (Magnetic Resonance) maps of different types for the organ;

a memory for storing each of the acquired quantitative MR maps;

a control unit including a processor, said control unit being configured for automatically estimating the maturation stage of the organ of the subject;

said control unit being configured for applying a function trained by a machine learning algorithm to the acquired quantitative MR maps in order to output an estimation of the maturation stage of the organ, the several quantitative MR maps being applied as input to the trained function for calculation of the age;

said control unit being configured to apply to each of the acquired quantitative MR maps a segmentation process configured for segmenting said biological organ into different regions each characterized by a single organ tissue type;

said trained function being configured to calculate a characteristic quantitative value for each region of the organ within each of said quantitative MR maps, said trained function being trained to estimate the organ maturation stage from the characteristic quantitative value determined for each region or a set of preferred regions;

said segmentation process being applied before applying the trained function; and a display for displaying the estimated maturation stage obtained for the organ.

11. The system according to claim 10, wherein said control unit is configured for training the function.

12. The system according to claim 10, wherein said control unit is configured for automatically calculating a difference between the estimated maturation stage of the organ or its estimated age, and a real age of the organ corresponding to an age of the subject, and said display is configured for automatically displaying the difference.

* * * * *

UNITED STATES PATENT AND TRADEMARK OFFICE
CERTIFICATE OF CORRECTION

PATENT NO. : 12,217,426 B2
APPLICATION NO. : 17/207963
DATED : February 4, 2025
INVENTOR(S) : Gian Franco Piredda et al.

It is certified that error appears in the above-identified patent and that said Letters Patent is hereby corrected as shown below:

In the Claims

Claim 5, Column 9, Line 54 to Column 10, Line 7 should read as follows:
automatically creating an input training dataset, wherein
    a segmentation process is applied to each quantitative
    MR map, the segmentation process being configured to
    classify the different tissues included within the organ
    in order to segment the organ into different regions,
    each region characterized by a single organ tissue type,
    at least one characteristic quantitative value being
    determined for at least one each region of each quantitative MR
    map being determined from the voxels of the quantitative MR map, for
    each of the quantitative MR maps, and the input training dataset being
    populated with the characteristic quantitative values obtained for each
    region of each quantitative MR map;
training a function based on the input training dataset and
    the output dataset with a training computation unit.
    using the several quantitative MR maps as input to the
    trained function for calculation of the age, the function
    being trained to estimate the organ maturation stage
    from the characteristic quantitative value(s) determined
    for at least one of the regions each region, or a set of preferred regions,
    and from the age of the subject for which the characteristic quantitative
    value has been obtained;

Claim 8, Column 10, Lines 35-39 should read as follows:
8. The computer-implemented method according to claim
5, which further comprises reducing a number of regional
characteristic quantitative values under consideration to
eliminate any correlation between characteristic quantitative Signed and Sealed this
Twenty-fifth Day of March, 2025

Coke Morgan Stewart
*Acting Director of the United States Patent and Trademark Office* values.

Claim 9, Column 10, Line 53 to Column 11, Line 7 should read as follows:
said training computation unit additionally configured to
    train and for training a function based on the input training dataset and the output dataset, the training using a machine learning algorithm configured for estimating the organ maturation stage, the several quantitative MR maps, being applied as input to the trained function for calculation of the age, the function being configured to calculate a characteristic quantitative value for each region of the organ within each quantitative MR map, and the function being trained to estimate the organ maturation stage from the characteristic quantitative value determined for each region or a set of preferred regions;